United States Patent
Stefan et al.

(10) Patent No.: US 9,655,636 B2
(45) Date of Patent: May 23, 2017

(54) MEDICAL INSTRUMENT

(71) Applicant: Karl Storz GmbH & Co. KG, Tuttlingen (DE)

(72) Inventors: Jochen Stefan, Wald (DE); Daniel Kärcher, Radolfzell (DE)

(73) Assignee: Karl Storz GmbH & Co. KG, Tuttlingen (DE)

( * ) Notice: Subject to any disclaimer, the term of this patent is extended or adjusted under 35 U.S.C. 154(b) by 109 days.

(21) Appl. No.: 14/618,590

(22) Filed: Feb. 10, 2015

(65) Prior Publication Data

US 2015/0230814 A1 Aug. 20, 2015

(30) Foreign Application Priority Data

Feb. 19, 2014 (DE) ........................ 10 2014 102 097

(51) Int. Cl.
*A61B 17/00* (2006.01)
*A61B 18/00* (2006.01)
*A61B 17/285* (2006.01)
*A61B 17/3201* (2006.01)
*A61B 18/12* (2006.01)

(52) U.S. Cl.
CPC ........ *A61B 17/285* (2013.01); *A61B 17/3201* (2013.01); *A61B 18/12* (2013.01); *A61B 2017/00371* (2013.01); *A61B 2017/00393* (2013.01); *A61B 2017/00424* (2013.01); *A61B 2018/00589* (2013.01); *A61B 2018/00952* (2013.01)

(58) Field of Classification Search
CPC ... A61B 17/285; A61B 17/3201; A61B 18/12; A61B 2017/00371
See application file for complete search history.

(56) References Cited

U.S. PATENT DOCUMENTS

2013/0310813 A1* 11/2013 Kaercher ............... A61B 17/00
606/1

FOREIGN PATENT DOCUMENTS

| DE | 9418094 U1 | 1/1995 |
| DE | 19780579 B4 | 4/2008 |
| DE | 102011085512 A1 | 5/2013 |
| DE | 102012007649 A1 | 10/2013 |
| EP | 2316358 B1 | 1/2012 |
| EP | 2532315 A1 | 12/2012 |

* cited by examiner

*Primary Examiner* — Sean Dougherty
(74) *Attorney, Agent, or Firm* — Whitmyer IP Group LLC

(57) ABSTRACT

A medical instrument with a handle arranged at the proximal end, with a shank arranged on the handle, and with a tool arranged at the distal end of the shank. The medical instrument can provide several functionalities, for example the rotation about the longitudinal axis of the medical instrument, the pivoting of the tool relative to the longitudinal axis of the medical instrument and/or the actuation of the tool, for example the opening or closing of scissors. Some of these functionalities are activated with the aid of a single common actuation element. By moving the actuation element between several switch positions, different functionalities are selected, and these are activated, e.g. by rotation of the actuation element.

18 Claims, 4 Drawing Sheets

MEDICAL INSTRUMENT

FIELD OF THE INVENTION

The invention relates to a medical instrument with a handle arranged at the proximal end, with a shank arranged on the handle, and with a tool arranged at the distal end of the shank.

BACKGROUND OF THE INVENTION

In addition to the simple medical instruments with one functionality, e.g. the opening and closing of scissors as a tool, more recent developments have resulted in medical instruments that have several different functionalities. The German patent DE 197 80 579 B4, for example, discloses a pivotable endoscopic instrument which has a tool in the form of a forceps-like gripping element and which has a second functionality that allows the distal end with the tool to be swiveled relative to the rest of the endoscopic instrument. For actuation of the two functionalities, dedicated actuation devices are provided which are separate from each other and which are arranged at the proximal end of the endoscopic instrument. This arrangement of the actuation elements provided sufficiently good handling and operating efficiency. The increased number of functionalities meant that the range of use of the endoscope was extended and, in this way, the surgical effort during the endoscopic operation was lessened, in particular by a reduction of the insertion and removal from the body.

This development was pursued and led to a medical instrument that has more than two functionalities. This is a tool that is opened and closed and that permits a rotation of the tool and also a pivoting of the distal end with the tool relative to the rest of the medical instrument. Each of these functionalities is operated by a dedicated actuation device at the proximal end. Such an instrument is known from the German laid-open specification DE 10 2012 007 649 A1. This instrument proves very versatile in terms of its possible uses during an endoscopic operation, but it requires thorough training of the operator in order to ensure reliable and safe handling especially under difficult operating conditions.

Furthermore, the European patent EP 2 316 358 B1 discloses a medical instrument with two functionalities that can be controlled in alternation via a single common actuation element. The actuation element is movable to two switch positions, wherein the actuation element is movably coupled to the shank in a first switch position and is movably coupled to the tool in a second switch position, and, therefore, it can either rotate the shank or can open or close the tool. The actuation element has a selector shaft with two coupling parts and, depending on the switch position, the respective coupling part couples with a form fit to one of two mating coupling parts and thus creates the possibility, by actuating the actuation element via the selector shaft with the coupling part coupled with a form fit to the mating coupling part, of transmitting a movement to the tool for opening or closing thereof or to the shank for rotation thereof. This medical instrument has improved ergonomics but is open to improvement in terms of the safety of its handling. This medical instrument of the type in question was used to draw up the preamble.

SUMMARY OF THE INVENTION

One object of the present invention is to make available a medical instrument that has improved ergonomics and operating safety along with more than one functionality.

This object according to the invention is achieved by a medical instrument. Advantageous developments are also disclosed.

The medical instrument according to the invention has a handle arranged at the proximal end, on which handle a shank is arranged, and a tool, in particular scissors, forceps or an HF coagulation tool, is arranged at the distal end of the shank. The handle has an actuation element with a selector shaft which, together with the actuation element, is movable at least to two switch positions. In a first switch position, which is provided for the activation of a first functionality, the selector shaft is movably coupled by form-fit engagement via a first coupling part to a first mating coupling part of a first output for the activation of the first functionality, whereas, in a second switch position for the activation of a second functionality, the selector shaft is movably coupled by form-fit engagement via a second coupling part to a second mating coupling part of a second output for the activation of the second functionality. In this way, depending on the switch position, a movement of the actuation element in the handle can be transmitted via the selector shaft to the first output or the second output and, in this way, the respective functionality of the instrument can be actuated. The medical instrument according to the invention is not limited to only two different switch positions for the activation of selective functionalities, and instead it is also possible for more than two different functionalities to be activated by different switch positions.

According to the invention, at least one part of the coupling parts has at least one resilient locking element which is designed to be able to couple with a form fit to a corresponding recess on the associated mating coupling part. Preferably, several resilient locking elements are provided which can engage in several corresponding recesses. Alternatively to this, it is also possible, according to the invention, that at least one of the mating coupling parts has one or more resilient locking elements which, in a corresponding way, are able to couple with a form fit to corresponding recesses on the corresponding coupling part of the selector shaft. By virtue of this inventive resilient design of the locking elements, the handling and therefore also the ergonomics of the medical instrument can be improved, since the introduction of the resilient locking elements into the corresponding recess to establish the form-fit engagement in the relevant switch position can be done more easily and, in particular, more comfortably in the force profile. In addition, the resilient design of the locking elements permits a particularly reliable form fit, which has a very positive effect on the safety of the medical instrument during handling, in particular under difficult operating conditions. It has thus been possible to keep to a minimum the number of actuation elements needed for the actuation of several functionalities and thus to maintain the ergonomics and maneuverability of the medical instrument at a high level.

It has proven particularly expedient for the resilient locking elements to be arranged in a seat in a coupling part or mating coupling part so as to be movable with a spring action, such that the resilient locking elements in the seat can be moved in the direction of or away from the center axis of the shank, i.e. in a radial direction, and can thus be moved into form-fit engagement in a corresponding recess or moved out of the latter. By means of the preferred guiding of the movement of the resilient locking elements by the seat, it is possible for several pairs of resilient locking elements and associated seats to be arranged in a very compact circle about the center axis of the shank in a coupling part or mating coupling part, which leads to a very compact and safe coupling by means of form-fit engagement, which thus transmits the movement of the actuation element very safely and reliably to the output for the actuation of the corresponding functionality. By virtue of the resilient design of the locking elements, which allows the locking elements to be pressed flexibly by a spring into the corresponding seats, it is possible, according to the invention, on the one hand in the coupled state, to insert the locking element as deep as possible into the seat, in particular as far as the bottom thereof, and thereby to achieve a very safe form-fit coupling, and, on the other hand, when necessary, to move the locking element back into the recess counter to the spring force and thus create flexibility and safety during the switching procedure, which is not found in the prior art with rigid locking elements and recesses.

By providing an abutment to limit the in particular radial mobility of the resilient locking elements, it is possible to ensure the safety of the medical instrument while at the same time maintaining the advantageous ergonomics, since a sliding out and therefore separation of the movable locking element from the seat and thus the risk of loss is prevented. The abutment is embodied in particular by formation of a narrowing in the seat, which narrowing effects a limitation of the movable locking elements. By the provision of spring elements to embody the resilient locking elements, an arrangement is created which, in particular by spring force, moves the resilient locking elements in the direction of the abutment by spring force. In the state of maximum excursion of the locking elements, secure engagement in the associated corresponding seat is permitted.

In addition to the possibility of forming the abutment by an additional structural part in the coupling part or mating coupling part, it has proven particularly expedient to form the abutment and the coupling part or mating coupling part in one piece, which increases the stability of the whole part and thus improves the safety of the medical instrument according to the invention. It has proven advantageous to provide not just one abutment for limiting the movement of the resilient locking element, but two such abutments between which the locking element can move freely under the action of a spring. The abutment on the spring side is chosen such that the spring is preferably only partially compressed, such that damage to the spring can be prevented. In addition to the provision of a compression spring, it is also alternatively possible to provide a tension spring with suitably adapted abutments or also an elastomer spring element.

By virtue of the preferred design of the selector shaft with recesses and/or resilient locking elements arranged rotationally symmetrically about the circumference of the selector shaft, it is possible to keep the material load of the selector shaft low and thereby ensure the reliability and stability of the function of the instrument according to the invention to a particular degree. It has proven particularly advantageous to provide three or four resilient locking elements or recesses in each coupling part of the selector shaft, which is arranged rotationally symmetrically, i.e. uniformly about the circumference of the selector shaft or the coupling part thereof. This particularly advantageous number of coupling elements for form-fit engagement on a coupling part or correspondingly on the mating coupling part permits a very efficient, optimized force distribution along with reduced manufacturing outlay. This arrangement proves surprisingly safe and its handling is very ergonomic.

Alternatively or additionally, it has also proven particularly expedient for the selector shaft to be designed with mirror symmetry, such that its two ends with the coupling parts are designed in mutual mirror symmetry to each other. The manufacturing quality and therefore the safety of the medical instrument can be additionally increased in this way, since the number of different structural parts is reduced and, therefore, the manufacture is simplified and thus the risk of incorrect function is reduced and thus the safety of the medical instrument is increased.

By the advantageous provision of a tapering in the end area of the selector shaft, it is possible in a particularly advantageous way, when transferring the actuation element with the selector shaft from one switch position to the other, to achieve a secure positioning of the coupling parts in the mating coupling parts, since the tip formed by the tapering permits an advantageous orientation, particularly in conjunction with a correspondingly tapering recess in the area of the mating coupling. It is thus possible to avoid the selector shaft being damaged by jamming in the area of the switch positions. Such a tapering is preferably provided at each end of the selector shaft.

By the provision of a rotary wheel or a cam as part of the actuation element, the possibility is afforded of moving and actuating the actuation element very easily and reliably by hand and therefore ergonomically safely. The actuation element can be actuated in different ways, for example by rotation but also by axial movement, such that, on the one hand, it is possible to use one of the actuation types to choose the switch position and thus the desired functionality of the medical instrument according to the invention, and to use the other actuation mode to activate and thus actuate the functionality of the medical instrument in the desired manner.

The provision of a rotary wheel permits, for example, practically blind actuation by rotation to any desired positions, without the user having to cast a glance at the actuation element. This permits very simple handling. The provision of a single cam permits targeted gripping of the cam and very simple and differentiated actuation in the different actuation modes, which proves very functional and ergonomic after the cam is found. The provision of an alternative single cam additionally permits the preferred coupling of the actuation element to a motorized drive, since the drive is connected with a form fit to the cam and the movement of the motorized drive is in this way reliably transmitted to the actuation element. In addition to the possibility of a form-fit connection with the aid of the single cam, there are also further possibilities with several recesses and elevations. This form-fit connection between the motorized drive and the actuation element is preferably releasable.

The actuation element for transmitting movement to the outputs is preferably in each case rotatable about an in particular common rotation axis. In other words, depending on the switch position in which the actuation element is located, an individual defined output is always rotatable by a rotation of the actuation element, and therefore a defined functionality assigned to this output can be activated. More preferably, the actuation element is axially movable to its switch positions parallel to its rotation axis, as a result of which a very simple and reliable and therefore ergonomic operation is ensured.

In addition to the switch positions in which it is movably coupled to the outputs via the selector shaft, the actuation element can preferably also be movable to at least one further switch position, in which the actuation element is movably coupled to none of the outputs for a functionality. This creates a neutralization of the actuation element, which is of particular importance especially for checking the functionalities or for maintenance or for the disassembly or assembly of the medical instrument according to the invention. It is thereby possible to improve the permanent safety of the instrument according to the invention.

It has proven particularly advantageous to provide one or more recesses, in particular all the recesses, with a run-on surface which, as the distance from the switch position decreases, effects an increasing restoring force of the spring element engaging in the recess. This ensures a very good and reliable handling of the medical instrument according to the invention during the switching procedure. This design has the effect that, at the start of the transfer to a switch position, the resistance force, which arises from the fact that the locking element is shortened counter to the spring force upon contact with the selector shaft in the area of the corresponding recess, is low and thus a positioning can be very easily and reliably ensured, whereas, as the switch position is increasingly approached, the resistance is slowly increased by the design of the run-on surface and, in this way, a form-fit pressing of the locking elements into the recess and thus a very reliable form fit is ensured.

In addition, as a supplement or alternative to the run-on surface in the recess, it has proven particularly expedient to design the recess in such a way that, in the area of a switch position, a run-off surface is provided which, as the distance from the relevant switch position decreases, provides a decreasing restoring force of the locking element. In this way, it is possible to form a depression in the recess, which effects a locking action when the locking element resiliently engages in the depression-like recess. It is thus possible to achieve a haptic feedback of the safe attainment of the switch position, which improves the handling and ergonomics of the medical instrument according to the invention. The dimensions of the depression are adapted to the spatial conditions, in particular the size of the locking elements and the desired extent of haptic feedback. A deep depression, which permits a substantial insertion of the locking element into the depression and is associated with a strong deep gradient, leads to a distinct haptic feedback, whereas a shallow depression leads only to a low haptic feedback. In addition, the run-off surface leads to a dedicated positioning of the locking element relative to the selector shaft with the depression-shaped recesses, since the locking elements are pressed into the depression by the spring action and, in this way, a lateral thrust by the run-off surface is generated, which moves the selector shaft to the switch position. This supports the improved handling.

A particularly preferred embodiment of the medical instrument according to the invention has recesses and/or corresponding resilient locking elements, of which one, some or all are designed conically such that they taper laterally or widen laterally as the distance from the switch position decreases. With this conical, wedge-shaped design, it is possible to ensure that a slight lateral offset during the switching procedure, i.e. during the transfer to the switch position and thus an approximation to the switch position, on account of the positioning action of the conical design of the recesses or of the locking elements leads to a lateral movement, particularly in the form of a rotational repositioning. In this way, an undesired blocking or impeding of the switching procedure can be substantially ruled out, which particularly improves the safety and the maneuverability and ergonomics of the present medical instrument according to the invention.

It has proven particularly advantageous to design not just some of the locking elements with a conical shape, but to provide all the locking elements of a coupling part or mating coupling part, and additionally the corresponding recesses, with the corresponding conical shape, such that a particularly effective form-fit engagement is obtained, which permits high transmission of force. It is not necessary that all the locking elements or all the recesses are conical, and instead this can also be only partially the case, but also a combination of conically shaped and non-conically shaped corresponding elements is possible and is chosen according to requirements and manufacturing possibilities.

A particularly safe and easily maneuverable medical instrument according to the invention has a selector shaft which exclusively has recesses in its coupling parts, which recesses are arranged in particular rotationally symmetrically about the circumference of the selector shaft, and resilient locking elements corresponding to the recesses and/or on the mating couplings which are connected to the respective output for the actuation of the functionality of the medical instrument. With this design, it is possible for the selector shaft to be made compact and light, which makes the actuation by means of the actuation element simpler and safer. In addition, this selector shaft according to the invention proves not to be structurally complex. The inventive arrangement of the corresponding resilient locking elements in the mating coupling, which is not moved for the switching procedure, leads to a very robust and reliable arrangement that is less susceptible to defects and is easy to produce. In particular, it permits the modular production of the individual components, mating coupling with resilient locking elements and output and the production of the selector shaft with actuation element. Overall, this preferred design of the invention leads to a very compact, reliable and safe medical instrument, which is distinguished by special ergonomics.

It has also proven advantageous to design the medical instrument with the resilient switching gear in such a way that it is possible to choose preferably in pairs of alternatives either, on the one hand, the functionality rotation of the shank or of the tool and, on the other hand, actuation of the tool or, on the one hand, the functionalities rotation of the shank or of the tool and, on the other hand, the pivoting of the tool relative to the longitudinal axis of the medical instrument or the shank of the medical instrument. These combinations permit a particularly advantageous and efficient and ergonomic handling of the medical instrument. In addition, it has also proven expedient for the pivoting relative to the longitudinal axis of the medical instrument or of the shank to be combined with the alternative functionality of the tool actuation. The tool actuation has proven in particular to be the opening and closing of the tool, e.g. in the form of forceps or scissors, but also for example the handling of an HF tool, in particular by increasing the size of the HF loop electrode or reducing the size of the latter, or an additional excursion of the tool.

In other words, the medical instrument according to the invention with several functionalities is distinguished by the fact that it is possible to switch between these functionalities by means of an actuation element, in particular by movement of an actuation element, and that, in the different switch positions, different coupling parts and mating coupling parts engage in one another with a form-fit, since it is not rigid components that engage in one another with a form-fit, but at least partially movable components which are spring-mounted and at least partially ensure the form-fit engagement. By virtue of the flexible position-changing, form-fitting parts, the adoption of the switch position is made easier, without the form-fit action being impaired to any relevant extent. Thus, the medical instrument according to the invention proves to be of a particularly advantageous design in ergonomic terms. In addition, it also proves particularly safe to handle.

BRIEF DESCRIPTION OF THE DRAWINGS

The invention is described below with reference to an example in the figures. The invention is not limited to this example.

DETAILED DESCRIPTION OF THE INVENTION

Figure 1:
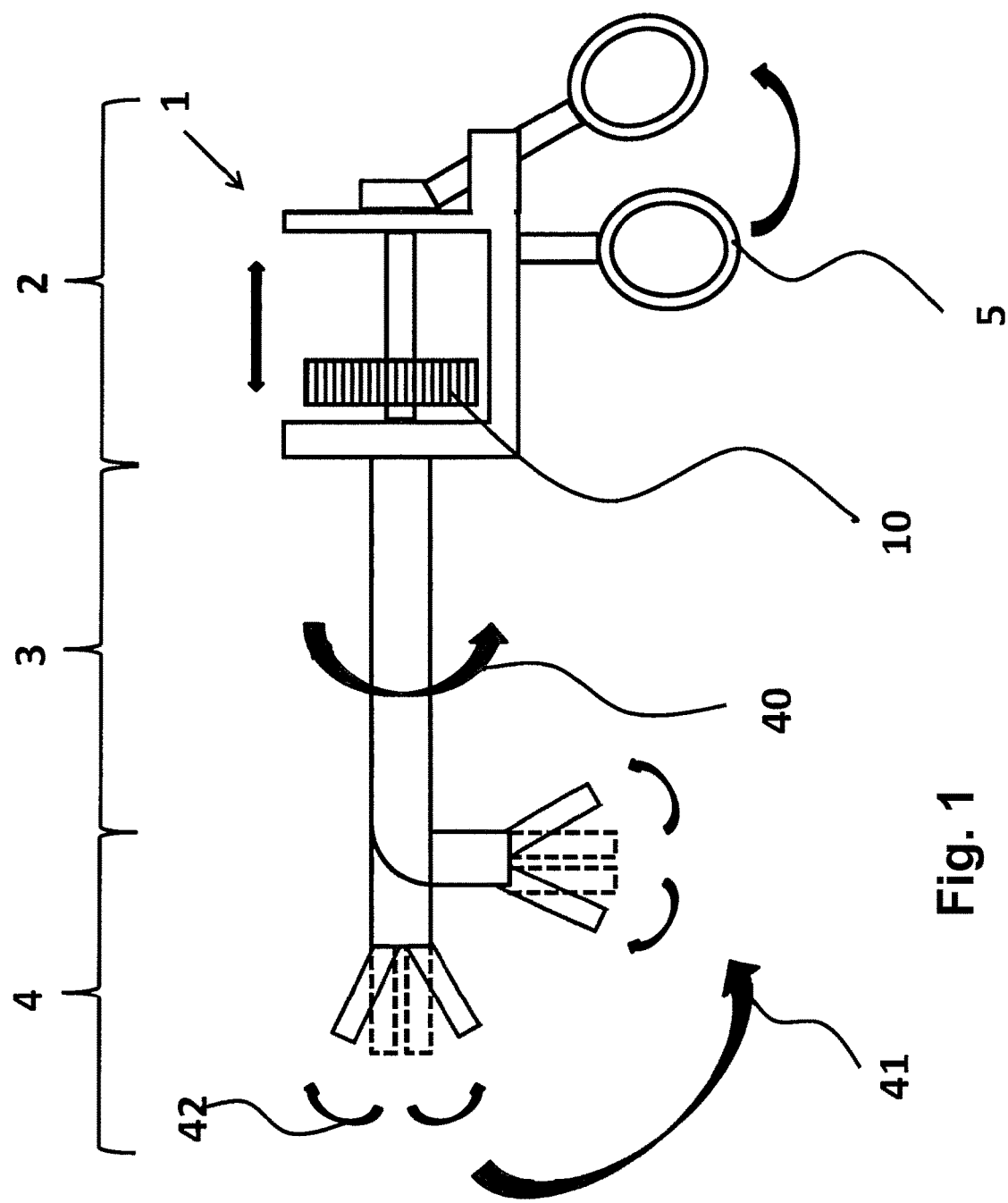
FIG. 1 shows an example of a medical instrument according to the invention in a side view.

The endoscopic medical instrument 1 shown by way of example in FIG. 1 has a handle 2, which is arranged at the proximal end of the medical instrument 1. The distal end of the handle 2 is adjoined by the shank 3, at the distal end of which the tool 4 is arranged in turn. The tool 4 is in the form of medical scissors or forceps with two jaw parts that can be moved toward and away from each other. This movement 42 of the tool 4 is represented by the indicated arrow 42. As a further functionality of the medical instrument 1, the distal end of the shank 3 with the tool 4 can be pivoted, this pivoting movement 41 being represented by the corresponding arrow 41. The pivoting takes place relative to the shank 3, which forms the main axis of the medical instrument 1. As a further functionality, the medical instrument 1 affords the possibility of moving the shank 3 in a rotation movement 40 in which the tool 4 with the shank 3 is moved in rotation about the longitudinal axis of the shank. This rotation movement 40 is represented by the rotation arrow 40.

The different functionalities can be controlled with the aid of the handle 2 at the proximal end of the medical instrument 1. The tool 4 is opened and closed with the aid of the grip 5. The functionality of the rotation movement 40 and of the pivoting movement 41 is controlled with the aid of the actuation element 10. The two movements 40 and 41 are controlled in alternation, wherein this takes place depending on the positioning of the actuation element 10, and the extent of the rotation movement 40 or of the pivoting movement 41 is defined by the rotation of the actuation element 10. The reduction in the means for actuating the medical instrument 1 satisfies an important condition for an efficient and ergonomic design of a medical instrument 1 with a plurality of functionalities 40, 41, 42.

Figure 2:
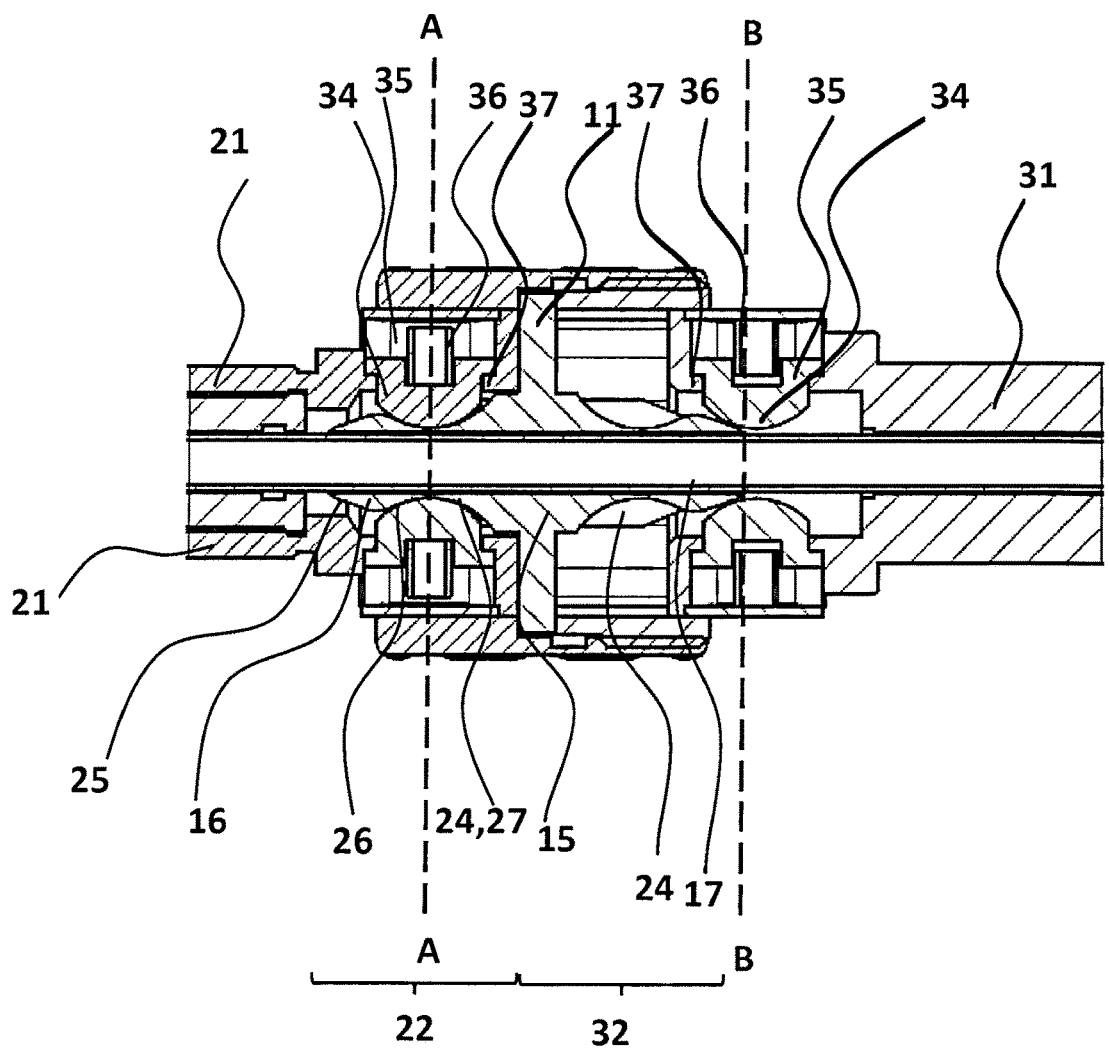
FIG. 2 shows a schematic longitudinal section through a part of the handle of a medical instrument according to the invention.

FIG. 2 shows a longitudinal section through a portion of a handle 2 in an embodiment of the invention.

The actuation element 10 has a radially protruding cam 11 which is provided for operating and actuating, on the one hand, an axial movement and, on the other hand, a rotation movement about the rotation axis of the actuation element 10. Moreover, the actuation element 10 has a selector shaft 15 which, together with the cam 11, forms the actuation element 10. The selector shaft 15 extends to both sides of the cam 11, which represents the center of the selector shaft 15. The selector shaft 15 has a symmetrical structure with respect to the cam 11, i.e. the first end 16 of the selector shaft 15 has the same structure as the second end 17 of the selector shaft 15, which ends extend to both sides of the cam 11. This results in a structurally simple configuration of the selector shaft 15, which increases the manufacturing reliability and thus the quality of the medical instrument 1.

The actuation element 10 can be moved axially between two switch positions. In the first switch position as shown in FIG. 2, the first end 16 of the selector shaft 15, with the first coupling part 22 arranged thereon, extends into a first mating coupling part 23, which is coupled to a first output 21 for transmitting the movement of the first coupling part 22 to the first output 21.

The first coupling part 22 of the selector shaft 15 has recesses 24 in which resilient locking elements 34, which are part of the first mating coupling part 23, engage with a form fit. This allows the rotation movement of the cam 11 to be transmitted, via the selector shaft 15 with the first coupling part 22 with its recesses 24, to the resilient locking elements 34 of the first mating coupling part 23 and thus to the first output 21. Thus, in the first switch position shown, the rotation movement 40 of the shank 3 and thus of the tool 4 can be activated with the aid of the cam 11.

In the first mating coupling part 23, which annularly encloses the first end 16 of the selector shaft 15 in the first switch position, the resilient locking elements 34 are arranged in seats 35. The seats 35 are formed as radially extending recesses in the first mating coupling 23, which allow the inserted resilient locking elements 34 to be guided in a radial movement. Also arranged in the seats 35 is a spring element 36, which applies a radial spring force to the resilient locking element 34. Both at the inner end of the seat 35 and also at the outer radial end of the seat 35, a respective abutment 37 is provided which limits the radial mobility of the resilient locking element 34. This ensures that the locking element 34 remains in the seat 35 and therefore in the first mating coupling 23, and the functionality of the resilient locking elements 34 is thereby ensured.

In the first switch position shown, the resilient locking element 34 engages with a form fit in the corresponding recess 24 of the first coupling part 22. The locking element 34 is pressed against the bottom of the recess 24 by the spring force of the spring element 36. The excursion of the resilient locking element 34, within the context of the mobility defined by the abutments 37, is dependent on an object arranged in the inner area of the first mating coupling part 23, which object is formed in the first switch position by the selector shaft 15 with the first coupling part 22.

At its first end 16, the first coupling part 22 has a conically tapering tip. When the selector shaft 15 is moved axially into the first switch position, the conically tapering first end 16 of the selector shaft 15 is thus inserted into the area between the locking elements 34 fully deflected by the spring elements 36. The locking elements 34 meet the cone of the tip and, as the distance of the selector shaft 15 from the first switch position decreases, are deflected less and less counter to the spring force until they slide into the recesses 24 and have then assumed the final excursion in the radial direction in the first switch position.

The flexible, situation-dependent positioning of the resilient locking elements 34 ensures very safe and comfortable handling of the medical instrument 1 upon adoption of the switch position. The conical profile of the first end 16 of the first coupling part 22 of the selector shaft 15 provides a slow increase in the resistance force against the adoption of the first switch position, which provides the safe and comfortable handling. This is also achieved by the fact that the bottom of the recess 24 has an area with a run-on surface which in accordance with the conically extending first end 16 of the selector shaft 15 increases the radius of the selector shaft 15 and thus forces the bearing locking element 34 back counter to the spring force of the spring element 36.

By the provision of a run-off surface 26 in the recess 24, the resilient locking element 34 can be locked in the recess 24 as soon as it reaches the first switch position. This is achieved by the fact that the radius of the selector shaft 15 decreases as the distance from the first end 16 of the selector shaft 15 increases, and therefore, when brought to the first switch position, with decreasing distance from this switch position, a decreasing restoring force of the resilient locking element 34 is provided since the latter can be more strongly deflected on account of the decreasing radius. This locking action gives the user haptic feedback that the first switch position is reached. Moreover, this run-off surface 26 has the effect that the adoption of this first switch position is supported by the spring force and, therefore, the adoption of this first switch position is made easier and, at the same time, the unwanted sliding out from this first switch position can be prevented on account of the increasing spring force during the movement out. This permits a very safe and comfortable ergonomically advantageous handling of the instrument 1 according to the invention with the switching between different switch positions.

The second end 17 with the second coupling part 32 of the selector shaft 15 has a structure corresponding to the first end 16 with the first coupling part 22. The same applies to the structure of the second mating coupling part 33, which corresponds to the first mating coupling part 23 and is movably coupled to the second output 31. It has the same arrangement of resilient locking elements 34 which are designed to be spring-loaded and radially movable in seats 35 by spring elements 36. Their radial mobility is likewise limited by abutments 37. In FIG. 2, the second mating coupling part 33 and the second coupling part 32 are shown in an uncoupled state. This state represents the first switch position. By axial movement of the actuation element 10 with the selector shaft 15, the selector shaft 15 leaves the first switch position shown, the form fit between the first coupling part 22 and the first mating coupling part 23 with their resilient locking elements 34 and the corresponding recesses 24 is canceled, the actuation element 10 is located in an intermediate position in which the selector shaft 15 is not movably coupled with a form fit either to the first mating coupling part 23 or to the second mating coupling part 33, and, consequently, cannot transmit any movement force to the two outputs 21, 31. If the actuation element 10 is moved further axially in the direction of the second mating coupling part 33, then, as has been described before accordingly for the first mating coupling part 23, it comes into form-fit engagement with the second mating coupling part 33 and thereby permits a movement transmission from the actuation element 10 to the second output 31 for the activation of the associated functionality.

The inventive resilient design of the locking elements 34 for the form-fit engagement in the associated, corresponding recesses 35 of the coupling parts 22, 32 or of the mating coupling parts 23, 33 ensures, on the one hand, a very safe and good transmission of force for the activation of the corresponding functionality of the medical instrument 1, since the spring force ensures a particularly good form fit, which is marked by the locking elements 34 bearing in the recesses 24. On the other hand, a very comfortable and ergonomically advantageous transfer of the actuation element 10 to the different switch positions is also achieved by the spring action, particularly in conjunction with the different designs of the selector shaft 15 with the different run-on surfaces 25 and run-off surfaces 26 and the conical design of the ends 16, 17 of the selector shaft 15. This leads overall to a very safe and ergonomically advantageous design of the medical instrument 1 according to the invention with a reduced number of actuation devices 10 on the handle 2 and a greater number of functionalities than the number of the actuation devices.

Figure 3:
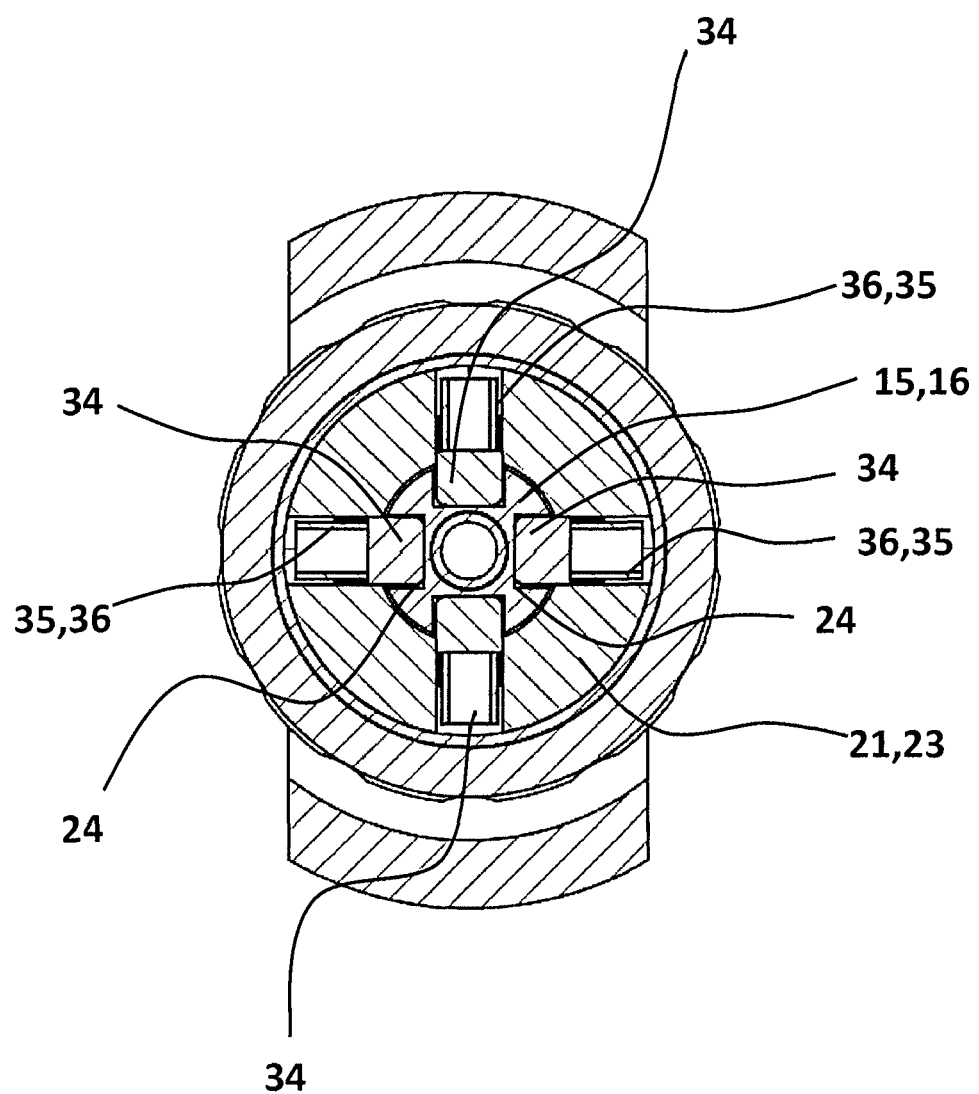
FIG. 3 shows a schematic cross section through a portion of the handle, along the section line A-A according to FIG. 2.

FIG. 3 shows a cross section through the first coupling part 22 and the first mating coupling part 23 in a first switch position along the section line A-A according to FIG. 2.

The first coupling part 22, which is arranged at the first end 16 of the selector shaft 15, has four recesses 24 which are arranged radially symmetrically and therefore uniformly about the circumference of the selector shaft 15 and which all have the same shape. Four resilient locking elements 34, which are part of the first mating coupling part 23, engage with a form fit in these four recesses 24. The resilient locking elements 34 are arranged in a ring-shaped housing of the first mating coupling part 23, in which for each locking element 34 there is a seat 35 that extends in the radial direction and has, at its respective radial end, an abutment 37 that limits the radial mobility of the resilient locking element 34. This prevents the locking element 34 from sliding out of or being lost from the first mating coupling part 23. A spring element 36, which is in the form of a compression spring, is provided in each of the seats 35. With the aid of its spring force, the spring element 36 presses the locking element 34 radially inward in the direction of the axis of rotational symmetry of the first mating coupling part 23. As is shown in FIG. 3, the radial mobility is limited by the bottom of the recesses 24 of the first coupling part 22. There, the resilient locking element 34 comes into abutment and thereby effects a very safe and reliable, form-fit coupling, which ensures a good transmission of force and transmission of movement from the actuation element 10 to the first output 21.

The first mating coupling part 23 has a structure composed of two rings which, inserted one into the other, form a common ring. The seats 35 are introduced as recesses with the inner abutment 37 into the inner ring. In the context of the production of the mating coupling part 23, a locking element 34 is first of all introduced into each of the seats 35 of the inner ring, followed by the associated spring element 36. Thereafter, this unit is introduced into the outer second ring, which has a closed configuration, such that a single common ring-shaped mating coupling part 23 is obtained. The outer ring thus forms the second radially outer abutment 37 for the spring element 36 or for the locking element 34. This design of the mating coupling part permits very safe and simple production for a medical instrument 1 according to the invention.

Figure 4:
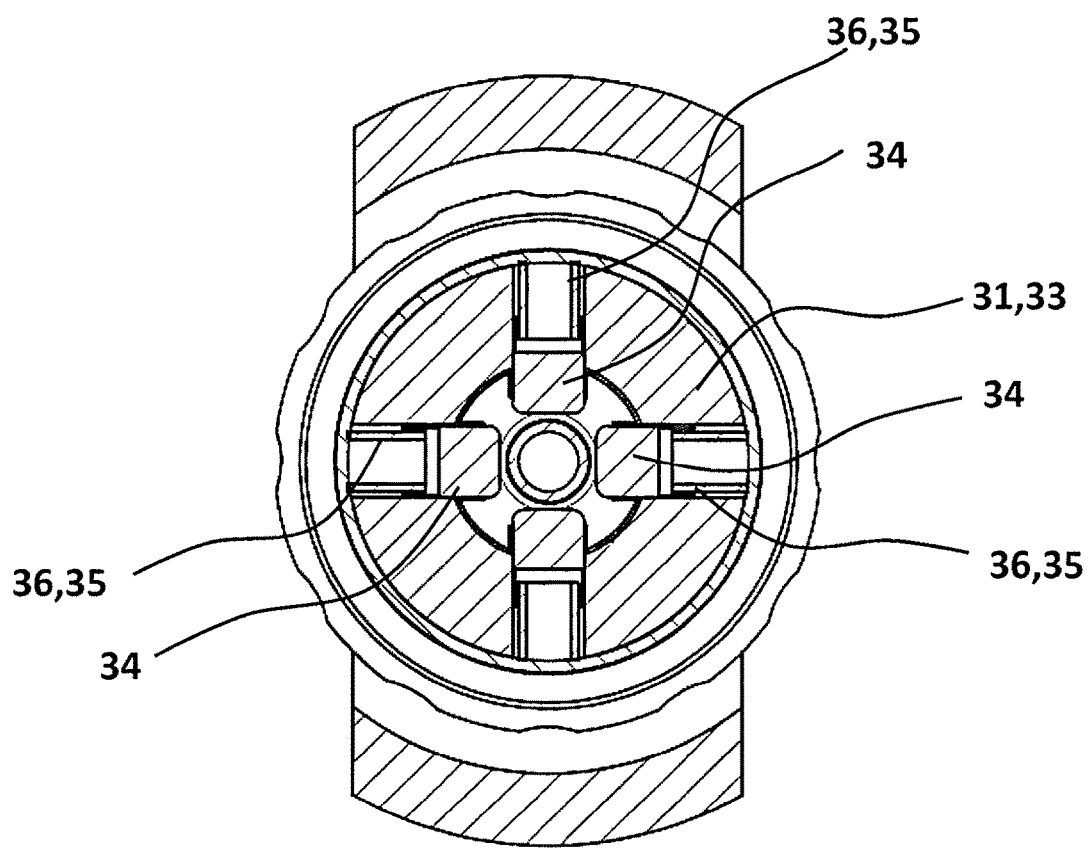
FIG. 4 shows another cross section through a part of the handle, along the section line B-B according to FIG. 2.

FIG. 4 shows a cross section through a second mating coupling part 33 during the first switch position from FIG. 2 along the section line B-B. It shows a structure corresponding to the first mating coupling part 23 of FIG. 2 and FIG. 3.

In contrast to FIG. 3, the resilient locking elements 34 are deflected further, since they are not limited in their radial excursion by the selector shaft 15. In this situation shown, no force transmission or movement transmission to the second output 31 can take place on account of the lack of form-fit engagement between actuation element 10 with the selector shaft 15 and the second mating coupling part 33. It is therefore clear that this first switch position, as is shown in FIG. 2, permits efficient, safe and ergonomically advantageous movement coupling to the first output 21 and thus for the activation of the associated functionality, namely the rotation of the shank 3, whereas at the same time, as is shown in FIG. 4, a movement coupling and to the second output 31 and thus an activation of the associated functionality, namely the pivoting of the tool 4 relative to the main axis of the medical instrument 1, is excluded. Axial movement of the actuation element 10 brings about, in the above-described advantageous and ergonomically comfortable and safe way, the connecting of the second coupling part 32 into the second mating coupling part 33 and therefore the attainment of the second switch position, which is associated with the uncoupling of the first coupling part 22 from the first mating coupling part 23. A transmission of movement is thus permitted by form-fit engagement of the resilient locking elements 34 in the associated, corresponding recesses 24 of the second coupling part 32, and thus a transmission of the rotating movement of the actuation element 10 to the second output 31 and thus an activation of the second functionality and thus an excursion of the tool 4 relative to the longitudinal axis of the medical instrument 1 or of the shank 3.

The invention claimed is:

1. A medical instrument with a handle arranged at a proximal end, with a shank arranged on the handle, and with a tool arranged at a distal end of the shank,
   wherein an actuation element, arranged on the handle, is movable to at least two switch positions and has a selector shaft,
   wherein, in a first switch position for activation of a first functionality, the actuation element is movably coupled to a first output and, in a second switch position for the activation of a second functionality, it is movably coupled to a second output of the medical instrument,
   wherein the selector shaft has a first coupling part which establishes a form fit with a first mating coupling part of the first output for the activation of a first functionality, and wherein the selector shaft has a second coupling part which establishes a form fit with a second mating coupling part of the second output for the activation of a second functionality,
   characterized in that
   the first and/or second coupling part has one or more resilient locking elements which are designed to be able to couple with a form fit to corresponding recesses on the respective first and/or second mating coupling part, and/or in that the first and/or second mating coupling part has one or more resilient locking elements which are designed to be able to couple with a form fit to corresponding recesses on the respective first and/or second coupling part.

2. The medical instrument according to claim 1, characterized in that resilient locking elements in a seat in the first and/or second coupling part or mating coupling part are designed to be movable resiliently in the radial direction.

3. The medical instrument according to claim 2, characterized in that the seat for a resilient locking element has an abutment for limiting mobility in a radial direction.

4. The medical instrument according to claim 1, characterized in that the selector shaft is rotationally symmetrical and/or both the proximal and distal ends with the coupling parts are designed in mirror symmetry to each other.

5. The medical instrument according to claim 1, characterized in that the selector shaft is designed tapering toward the proximal and/or distal ends.

6. The medical instrument according claim 1, characterized in that the actuation element has a rotating wheel or a cam for the actuation.

7. The medical instrument according to claim 1, characterized in that the actuation element is connected with a form fit to a motor-driven drive.

8. The medical instrument according to claim 1, characterized in that the actuation element for the movement transmission to the outputs is in each case rotatable about a common rotation axis and is axially movable to the first and second switch positions in the direction of the rotation axis.

9. The medical instrument according to claim 1, characterized in that the actuation element for movement transmission between the switch positions for the activation of different functionalities has one or more intermediate positions, which have no movement coupling to one of the outputs for a functionality.

10. The medical instrument according to claim 1, characterized in that one or more recesses have a run-on surface which, with a decreasing distance from the first and/or second switch position, effects an increasing restoring force of the resilient locking element.

11. The medical instrument according to claim 1, characterized in that one or more recesses have a run-off surface which, in the area of the first and/or second switch position, with a decreasing distance from the first and/or second switch position, effects a decreasing restoring force of the resilient locking element and, therefore, a locking action.

12. The medical instrument according to claim 1, characterized in that recesses and/or the corresponding resilient locking elements taper laterally and/or widen laterally with a decreasing distance from the first and/or second switch position.

13. The medical instrument according to claim 1, characterized in that 3 or 4 corresponding resilient locking elements and recesses are formed in or on the coupling parts or mating coupling parts.

14. The medical instrument according to claim 1, characterized in that corresponding recesses are arranged in the coupling parts of the selector shaft, and the corresponding resilient locking elements are arranged in or on the mating coupling parts.

15. The medical instrument according to claim 1, characterized in that switched outputs effect the tool actuation in particular by opening or closing, the pivoting relative to the longitudinal axis of the medical instrument and/or the rotation about the longitudinal axis of the medical instrument.

16. The medical instrument according to claim 1, characterized in that in the first switched position the first output activates rotation about the longitudinal axis of the medical instrument and in the second switched position the second output activates pivoting relative to the longitudinal axis of the medical instrument.

17. The medical instrument according to claim 1, characterized in that the first and second coupling part has one or more resilient locking elements which are designed to be able to couple with a form fit to corresponding recesses on the respective first and second mating coupling part to establish form fit engagement in the relevant switch position.

18. The medical instrument according to claim 1, characterized in that the first and second mating coupling part has one or more resilient locking elements which are designed to be able to couple with a form fit to corresponding recesses on the respective first and second coupling part to establish form fit engagement in the relevant switch position.

* * * * *